|   | United States Patent [19] | [11] | Patent Number: | 4,886,665 |
|---|---|---|---|---|
|   | Kovacs | [45] | Date of Patent: | Dec. 12, 1989 |

[54] COMPOSITIONS OF OATS AND NETTLE EXTRACTS TO BE USED AS A FOOD ADDITIVE OR PHARMACEUTICAL PREPARATION IN HUMAN HEALTH CARE

[75] Inventor: Joseph Kovacs, Geneva, Switzerland

[73] Assignee: Arcopharma Ltd., Geneva, Switzerland

[21] Appl. No.: 24,446

[22] Filed: Mar. 11, 1987

[51] Int. Cl.⁴ ................... A61K 35/78; A23L 1/28; B09B 3/00

[52] U.S. Cl. ................... 424/195.1; 514/783; 424/439; 424/442; 426/655

[58] Field of Search ............ 424/195.1, 439, 442; 514/783; 426/655

[56] References Cited

U.S. PATENT DOCUMENTS 4,518,789 5/1985 Yu et al. .................... 514/859
4,716,120 12/1987 Tsay et al. ................ 424/195.1

OTHER PUBLICATIONS

Monograph–British Herbal Pharmacopoeia (1976), pp. 27 and 217.
Fukushima et al., Tohoku J. Exp. Med., 1976, vol. 119, pp. 115–122.

*Primary Examiner*—Ronald W. Griffin
*Attorney, Agent, or Firm*—Beveridge, DeGrandi & Weilacher

[57] ABSTRACT

A food supplement composition is described containing an oat extract and an extract of nettle (Urtica). The combined extracts can be in the form of powder which is added to a beverage or any fruit juice to provide a nutritional drink. The composition can also be used for the treatment of a dysfunction of a warm blooded mammal. The products can be taken in various forms such as dried powdered mix with a liquid, as a pill, tablet, capsule, or for nasal delivery.

15 Claims, No Drawings

COMPOSITIONS OF OATS AND NETTLE EXTRACTS TO BE USED AS A FOOD ADDITIVE OR PHARMACEUTICAL PREPARATION IN HUMAN HEALTH CARE

INTRODUCTION AND BACKGROUND OF THE INVENTION

The present invention relates to compositions in which substances of plant or botanical origin are present which substances have important metabolic properties and functions for use in connection with human health care. More particularly, the present invention relates to extracts of oats and nettle plants and food supplement compositions containing same, pharmaceutical preparations containing these extracts and methods for using same.

The plant known as Avena sativa L. (Fam. Gramineae), or more commonly known as oats, has been known in the past for its therapeutic properties. As described in the British Herbal Pharmacopoeia, published by the British Herbal Medicine Association 1976, part 1, page 27, avena consists of the dehusked and rolled starchy seed endosperm of Avena sativa L. (Fam. Gramineae). This product contains much starch, some protein and a little fat which contains some tocopherol. It is a creamy white and buff, flaky mass with a mealy taste. It consists of mainly starch in ovate compound grains of 2 to many rounded-poly-hedral grains, with many single grains of which some are lemon- or spindle-shaped, the individual grains being from 3 to 12 μm. On clearing the starch, oil globules are visible, and an aleurone layer of thick-walled cells with granular contents adjoining a layer of thin-walled, elongated cells in which occur a few thick-walled, small, circular cells. U.S.D., 22nd Edn., p. 208-9.

The nettle plant is more precisely referred to as Urtica (Stinging Nettle) and consists of the dried aerial parts of Urtica dioica L. (Fam. Urticaceae) which is gathered during the flowering period. The plant is a native British herb which may be up to 150 cm tall. It is upright and has stinging hairs with ovate, usually cordate, toothed leaves bearing insignificant axillary heads of green flowers.

Urtica contains indolic compounds including histamine and 5-hydroxytryptamine and various acids including ascorbic acid.

The cut herb has leaf pieces wrinkled and rolled of various shades of dark green, bearing obvious stinging hairs. Stem pieces are ridged, hollow, perhaps split, hairy, and pale green-brown in appearance. It may cause a skin irritation if handled.

As described in the British Pharmacopoeia, p. 217, the microscopical appearance is:

Covering trichomes unicellular, up to 700 μm long, slender and conical, often curved. Glandular trichomes, few, over veins, on the lower surface, with short unicellular stalks, and small, rounded heads of 2 to 4 cells. Stinging hairs unicellular, elevated on a multiseriate base, conical, up to 2 mm long, thick-walled, pointed, with an apex which is readily broken away, very birefringent. Leaf epidermis with sinuous anticlinal walls, some cells containing dense, granular, non-birefringent cystoliths of calcium carbonate. Stomata anomocytic. Calcium oxalate clusters, small, scattered, birefringent.

It is reported to be anti-haemorrhagic and have hypoglycaemic properties.

In a recent publication by K. Schmidt in Fortschr. Med., 101, pp. 713-716 (1983), the action of radix urticae extracts on sexual hormone binding globulin of the blood plasma in benign prostatic hyperplasia was demonstrated. The study refers to the interaction of an extract of radix urticae with sexual hormone binding globulin of the blood plasma and with androgen receptor of the prostatic cytosol. It was shown that the binding of 5-alpha-dihydrotestosterone with the binding protein can be influenced by the extract of radix urticae (nettle root).

As disclosed by Fukushima et al in the Tohoku J. exp. Med., 1976, Vol. 119, pp. 115-122, Avena sativa can be extracted and treated to obtain a purified substance with luteinizing hormone (LH) releasing activity. In carrying out this process, the young oat leaves are passed through a food chopper and then treated in hot distilled water for a period of time. The oat leaf extract is then collected, adjusted to pH of 5.7 with acetic acid and then filtered into a chromatographic column.

The substance was demonstrated to have a luteinizing hormone releasing activity by the ovarian ascorbic acid depletion method using Wistar-Imamichi strain rats. The evidence in the Journal was that the action is in adenohypophysis. The experiments reveal that extracts of oats are capable of potentiating lordotic behavior in the ovariectomized, estrogen primed female rat. The potentiation of behavior can be obtained with a dose as small as 0.25 cc of substance injected subcutaneously. It does not possess estrogenic activity in that the oats extract cannot be substituted for estrogen priming to obtain mating behavior. The facilitation of sexual behavior begins approximately five hours after subcutaneous administration and lasts until approximately eight hours of administration. It has been found to increase plasma LH levels at 10 minutes post-IV infusion. It has been observed to increase plasma follicle stimulating hormone FSH levels at 10 and 20 minute post-infusion intervals while it had no consistent effect on plasma prolactin PRL levels.

It is an object of the present invention to provide compositions comprising oats and nettle extracts suitable for use as a food supplement.

It is a further object of the present invention to provide pharmaceutical formulations containing oats and nettle extracts.

It is still a further object of the present invention to provide methods of treating conditions and/or dysfunctions in warm-blooded mammals, such as humans, utilizing formulations containing oats and nettle extracts.

SUMMARY OF THE INVENTION

In attaining the above and other objects, one feature of the present invention resides in a nutritional supplement for regular alimentary or external assimilation comprising a mixture of oats and nettle extracts, which may further contain other assimilable components constituting a food or conventional composition of known type.

A further feature of the present invention resides in incorporating the nutritional supplement comprising oats and nettle extracts into a food or drink composition containing 0.005-1% by weight of the extract composition.

Still further, it is a feature of the invention to provide a pharmaceutical composition for treatment or prevention of various disfunctions of the human body, for regular assimilation comprising oats and nettle extracts, optionally containing other assimilable components of conventional type. A pharmaceutically acceptable carrier is normally included in these compositions. Any conventional carrier may be used.

Yet another feature of the present invention resides in providing a treatment or prevention for a dysfunction such as a benign prostatic hyperplasia, sexual dysfunction, breast cancer, and high cholesterol level.

DETAILED DESCRIPTION OF THE INVENTION

The present invention relates to compositions containing extracts from oats and nettle (Urtica) as the essential ingredients and the preparation of food supplement compositions, compositions suitable for pharmaceutical use and methods of treating conditions using these compositions. More particularly, extracts of oats and extracts of nettle (Urtica) are blended to form a food supplement and may, in turn, be blended with a variety of additional plant derivatives or conventional ingredients. The extracts described herein can be obtained through modern extraction methods under rigorous quality controls. The extracts are usually prepared in powdered form and meet the specifications described in leading pharmacopoeias. They are biologically standardized according to such selected parameters as sugar content, ash, protein, acids and flavanoid concentration. The oats extracts can be derived by a variety of known methods such as shown by Fukushima et al, supra, the entire disclosure of which is incorporated herein and relied on. Classical methods described in the literature can be used to obtain the oats extract and the nettle extract.

In Galenical formulations, oats and nettle extracts are mixed in various proportions and supplemented with either natural Vitamin C from a hippophae fruit, or ascorbic acid or both. A large number of excipients can be used in powder mixes, nasal gels, drop or spray applications, in syrups, ointments or in a suppository.

The compositions of the present invention have been clinically tested in single dosage form as in a powder mix as shown in Example 1a.

The following examples serve to illustrate the present invention but are not limiting thereof:

EXAMPLE 1

Composition of single dose powder mix in packets:

|  | a | b | c |
|---|---|---|---|
| Oat extract | 300 mg | 150 mg | 250 mg |
| Nettle extract | 150 mg | 300 mg | 250 mg |
| Hippophae extract | 100 mg | 100 mg | 100 mg |
| Ascorbic acid | 100 mg | 100 mg | 100 mg |
| Glycine | 100 mg | 100 mg | 100 mg |
| Glucose | 100 mg | 100 mg | 100 mg |
| Calcium phosphate | 100 mg | 100 mg | 50 mg |
| Citric acid | 30 mg | 30 mg | 30 mg |
| Colloidal silica | 20 mg | 20 mg | 20 mg |
| TOTAL | 1000 mg | 1000 mg | 1000 mg |

|  | d |
|---|---|
| Oat extract | 250 mg |
| Nettle extract | 250 mg |
| Hippophae extract | 100 mg |
| Scutellaria extract | 100 mg |
| Malt | 100 mg |
| Ascorbic acid | 50 mg |
| Glycine | 50 mg |
| Calcium phosphate | 50 mg |
| Citric acid | 30 mg |
| Colloidal silica | 20 mg |
| TOTAL | 1000 mg |

In the above formulation, any suitable commercially available colloidal silica for pharmaceutical purposes can be used. Any example of this is Aerosil ® made by Degussa AG.

EXAMPLE 2

Compositions of powder mix for capsules or tablets:

|  | a | b | c | d |
|---|---|---|---|---|
| Oat extract | 300 mg | 150 mg | 250 mg | 250 mg |
| Nettle extract | 150 mg | 300 mg | 250 mg | 250 mg |
| Hippophae extract | 100 mg | 100 mg | 100 mg | — |
| TOTAL | 550 mg | 550 mg | 600 mg | 500 mg |

|  | e |
|---|---|
| Oat extract | 250 mg |
| Nettle extract | 250 mg |
| Scutellaria extract | 50 mg |
| Hippophae extract | 50 mg |
| TOTAL | 600 mg |

EXAMPLE 3

Compositions for nasal delivery forms (gel, drop, spray):

|  | a | b | c |
|---|---|---|---|
| Oat extract | 30 mg | 15 mg | 25 mg |
| Nettle extract | 15 mg | 30 mg | 25 mg |
| Hippophae extract | 10 mg | 10 mg | — |
| Excipients | 45 mg | 45 mg | 50 mg |
| TOTAL | 100 mg | 100 mg | 100 mg |

|  | d |
|---|---|
| Oat extract | 30 mg |
| Nettle extract | 15 mg |
| Vitamin E | 10 mg |
| Excipients | 45 mg |
| TOTAL | 100 mg |

|  | e |
|---|---|
| Oat extract | 25 mg |
| Nettle extract | 25 mg |
| Scutellaria extract | 10 mg |
| Excipients | 40 mg |
| TOTAL | 100 mg |

Further variations and modifications of the foregoing invention will be apparent to those skilled in the art and are intended to be encompassed by the claims appended hereto.

I claim:

1. A nutritional supplement for regular alimentary or external assimilation comprising an admixture of oats and nettle (Urtica) extract.

2. The nutritional supplement according to claim 1 which additionally contains one or more conventional food ingredients.

3. The nutritional supplement according to claim 1 which additionally contains a hippophae extract.

4. The nutritional supplement according to claim 1 which contains one or more of ascorbic acid, glycine, glucose, calcium phosphate, citric acid, colloidal silica.

5. The nutritional supplement according to claim 1 comprising a powder mix of the following formulation:

| | |
|---|---|
| Oat extract | 300 mg |
| Nettle extract | 150 mg |
| Hippophae extract | 100 mg |
| Ascorbic acid | 100 mg |
| Glycine | 100 mg |
| Glucose | 100 mg |
| Calcium phosphate | 100 mg |
| Citric acid | 30 mg |
| Colloidal silica | 20 mg |
| TOTAL | 1000 mg. |

6. The nutritional supplement according to claim 1 comprising a powder mix of the following formulation:

| | |
|---|---|
| Oat extract | 150 mg |
| Nettle extract | 300 mg |
| Hippophae extract | 100 mg |
| Ascorbic acid | 100 mg |
| Glycine | 100 mg |
| Glucose | 100 mg |
| Calcium phosphate | 100 mg |
| Citric acid | 30 mg |
| Colloidal silicon dioxide | 20 mg |
| TOTAL | 1000 mg. |

7. The nutritional supplement according to claim 1 comprising a powder mix of the following formulation:

| | |
|---|---|
| Oat extract | 250 mg |
| Nettle extract | 250 mg |
| Hippophae extract | 100 mg |
| Ascorbic acid | 100 mg |
| Glycine | 100 mg |
| Glucose | 100 mg |
| Calcium phosphate | 50 mg |
| Citric acid | 30 mg |
| Colloidal silicon dioxide | 20 mg |
| TOTAL | 1000 mg. |

8. The nutritional supplement according to claim 1 comprising a powder mix of the following formulation:

| | |
|---|---|
| Oat extract | 250 mg |
| Nettle extract | 250 mg |
| Hippophae extract | 100 mg |
| Scutellaria extract | 100 mg |
| Malt | 100 mg |
| Ascorbic acid | 50 mg |
| Glycine | 50 mg |
| Calcium phosphate | 50 mg |
| Citric acid | 30 mg |
| Colloidal Silicon dioxide | 20 mg |
| TOTAL | 1000 mg. |

9. The nutritional supplement according to claim 1 comprising a powder mix of the following formulation:

| | |
|---|---|
| Oat extract | 300 mg |
| Nettle extract | 150 mg |
| Hippophae extract | 100 mg |
| TOTAL | 550 mg. |

10. The nutritional supplement according to claim 1 comprising a powder mix of the following formulation:

| | |
|---|---|
| Oat extract | 150 mg |
| Nettle extract | 300 mg |
| Hippophae extract | 100 mg |
| TOTAL | 550 mg. |

11. The nutritional supplement according to claim 1 comprising a powder mix of the following formulation:

| | |
|---|---|
| Oat extract | 250 mg |
| Nettle extract | 250 mg |
| Hippophae extract | 100 mg |
| TOTAL | 600 mg. |

12. The nutritional supplement according to claim 1 comprising a powder mix of the following formulation:

| | |
|---|---|
| Oat extract | 250 mg |
| Nettle extract | 250 mg |
| TOTAL | 500 mg. |

13. The nutritional supplement according to claim 1 comprising a powder mix of the following formulation:

| | |
|---|---|
| Oat extract | 250 mg |
| Nettle extract | 250 mg |
| Scutellaria extract | 50 mg |
| Hippophae extract | 50 mg. |
| TOTAL | 600 mg. |

14. A beverage composition containing 0.005-1% by weight of the nutritional supplement according to claim 1.

15. A pharmaceutical composition comprising an oats extract, a nettle (Urtica) extract and a pharmaceutically acceptable carrier therefor.

* * * * *